United States Patent [19]

Gowan, Jr. et al.

[11] Patent Number: 5,405,617

[45] Date of Patent: Apr. 11, 1995

[54] ALIPHATIC OR FATTY ACID ESTERS AS A SOLVENTLESS CARRIER FOR PHARMACEUTICALS

[75] Inventors: Walter G. Gowan, Jr., Glenside; Richard D. Bruce, Abington, both of Pa.

[73] Assignee: McNeil-PPC, Inc., Milltown, N.J.

[21] Appl. No.: 790,613

[22] Filed: Nov. 7, 1991

[51] Int. Cl.$^6$ ................................. A61K 9/16
[52] U.S. Cl. .................... 424/464; 424/485; 424/496; 424/502; 424/484
[58] Field of Search ............ 424/476, 498, 484

[56] References Cited

U.S. PATENT DOCUMENTS

| | | | |
|---|---|---|---|
| 2,011,586 | 8/1935 | Miller | 424/476 |
| 4,151,273 | 6/1978 | Riegelman et al. | 424/78 |
| 4,199,576 | 4/1980 | Reller et al. | 424/230 |
| 4,460,602 | 7/1984 | Buckwalter et al. | 424/322 |
| 4,820,523 | 4/1986 | Shtohrya et al. | 424/469 |
| 4,948,622 | 8/1990 | Kokubo et al. | 427/3 |
| 5,013,759 | 5/1991 | Berman et al. | 514/622 |

FOREIGN PATENT DOCUMENTS

| | | |
|---|---|---|
| 0383406A1 | 2/1990 | European Pat. Off. . |
| 1056259 | 11/1965 | United Kingdom . |
| 1205769 | 7/1967 | United Kingdom . |

OTHER PUBLICATIONS

Gollamudi Ramachander, et al., "Effect of Salicylamide and Acetaminophen on Dextromethorphan Hydrobromide Metabolism: Possible Pharmacological Implications", pp. 761–764.

*Primary Examiner*—Thurman K. Page
*Assistant Examiner*—Neil Levy
*Attorney, Agent, or Firm*—Bernard F. Plantz

[57] ABSTRACT

A physicochemically stable pharmaceutical matrix composition is provided comprising: a pharmaceutical active and a water insoluble aliphatic or fatty acid ester, preferably stearyl stearate; a taste mask carrier for pharmaceutical actives comprising a taste masking effective amount of an aliphatic or fatty acid ester; and a method for preparing a pharmaceutical matrix without the use of organic and/or volatile solvents comprising the steps of: melting an aliphatic or fatty acid ester; admixing at least one pharmaceutical active with the molten aliphatic or fatty acid ester; and solidifying the admixture to produce a pharmaceutical matrix composition. The matrix is composed of an aliphatic, or fatty acid, ester that has a low melting point (50°–100° C.) and the melt exhibits: low viscosity, recongeals rapidly when cooled, does not exhibit polymorphism, and has good mold release properties.

14 Claims, No Drawings

ALIPHATIC OR FATTY ACID ESTERS AS A SOLVENTLESS CARRIER FOR PHARMACEUTICALS

FIELD OF THE INVENTION

This invention relates to providing a taste mask coating or carrier for pharmaceutical actives. More particularly, the coating or carrier comprises one or more aliphatic or fatty acid esters which may be applied without the use of organic solvents and a method for preparing coated pharmaceuticals and pharmaceutical products.

BACKGROUND OF THE INVENTION

Orally administered medicaments are given to patients in many forms such as liquid solutions, emulsions or suspensions or in solid form such as capsules or tablets (as used herein, the term "tablet" means any shaped and compressed solid dosage form, including caplets). Many medicaments require the use of volatile solvents in their preparations, usually organic solvents that may pose health and safety concerns for patients consuming such medicaments and plant personnel producing such medicaments. The volatile solvents are generally undesirable components and/or impurities of the medicament compositions owing to their odor or deleterious effects upon ingestion. Volatile solvents also provide safety risks in production facilities particularly from explosions or inhalation by workers.

It is therefore desirable to provide a carrier system for pharmaceutical actives that does not require the use of organic solvents. Another characteristic desirable for carrier compositions for pharmaceutical actives is good physicochemical stability, i.e., resistance to changes including coalescence, molecular rearrangement, polymorphic changes, and other undesirable physicochemical interactions with pharmaceutical active compositions upon storage and aging.

Many medicaments administered in tablet and capsule form are intended to be swallowed whole. In these situations the often disagreeable taste of the active ingredient need not be taken into account in formulating the medicine, except for the provision of means of preventing the taste from being apparent during the short time that the medicine is in the mouth. Such means may include an appropriately thin and quickly dissolving coating on the tablet, the use of the gelatin capsule form, or simply compressing a tablet firmly enough so that it will not begin to disintegrate during the short time that it is intended to be in the mouth.

Children, older persons, and many other persons have trouble swallowing whole tablets and even capsules. Consequently, in cases where the dosage to be administered cannot be made into a very small tablet or capsule, it is desirable to provide the medicine in either liquid form or in a chewable solid form. Even when the medicine can be formulated as a liquid, it is desirable also to be able to provide a chewable solid form because it is usually more convenient to carry a supply of tablets than a container of liquid medicine.

A common problem with the chewable tablet form is the often disagreeable taste of the active ingredient which manifests itself during chewing. In some cases, the taste of the active medicament in a tablet can be overpowered by adding flavoring ingredients and/or sugar to the tablets.

There also exist various coating means by which a pharmaceutical active may be shielded by a coating while the tablet is in the mouth but becomes bioavailable later by permeation through the coating or the coating's dissolution in the gastrointestinal tract after the medicament has been swallowed. Examples of such coating systems are described for example in U.S. Pat. No. 4,851,226 which discloses chewable medicament tablets wherein the granules of active ingredient are coated with a blend of cellulose acetate or cellulose acetate butyrate and polyvinyl pyrrolidone (PVP).

The present invention is directed to the discovery of a solventless coating or carrier system which can achieve taste masking of pharmaceutical products which utilizes an edible and physicochemically stable carrier composition. This carrier composition is used to form a "matrix" which is defined herein as a solid composition comprising a carrier and/one or more pharmaceutical actives.

SUMMARY OF THE INVENTION

As embodied and fully described herein, the present invention provides a taste mask coating or carrier matrix for pharmaceutical actives comprising a taste mask effective amount of an aliphatic or fatty acid ester. Aliphatic esters or fatty acid esters, are defined herein as esters composed of a fatty acid and a fatty alcohol. These fatty acids and alcohols are usually saturated and have 12-22 carbon atoms. Unsaturated fatty acids or alcohols can be used in combination with saturated fatty acids or alcohols. Fatty acids and alcohols with less than 12 carbon units may be used in combination with higher carbon unit fatty acids or alcohols. However, formulations which contain unsaturated fatty acids or alcohols, or short chain fatty acids or alcohols, should be solid at room temperature.

In other embodiments of the invention a physicochemically stable pharmaceutical matrix composition is provided comprising pharmaceutical active(s) and an aliphatic or fatty acid ester carrier composition, preferably stearyl stearate. Many fatty acid esters, or aliphatic esters, exhibit polymorphism. This can result in a coating or matrix that exhibits polymorphic changes as the product ages or is exposed to elevated temperatures. These polymorphic changes can affect the product's performance and thus, are undesirable. This invention provides for a physicochemically stable pharmaceutical matrix or coating.

Many fatty acid esters, or aliphatic esters, are very viscous when melted. In the preferred embodiment of this invention, the aliphatic ester, or fatty acid ester, can be melted at 50°-100° C. and the resultant melt exhibits a low viscosity. The low viscosity of the melt greatly aids in further processing of the melt (mixing, pumping, spraying). In addition, other preferred characteristics are: rapid recongealing of the melt when cooled, no polymorphism, and good mold releasing characteristics. The above characteristics are exhibited by the preferred embodiment of this invention: stearyl stearate.

In further embodiments of the invention, a solventless method for preparing a pharmaceutical matrix is provided comprising the steps of: melting an aliphatic or fatty acid ester; admixing at least one pharmaceutical active with the molten aliphatic or fatty acid ester; and solidifying the admixture to produce a pharmaceutical matrix composition. In preferred embodiments of the method of the invention the aliphatic or fatty acid ester is selected from the group consisting of aliphatic or fatty acid esters, with melting points in the 50°-100° C. range; more preferably stearyl stearate. In preferred embodiments of the invention the pharmaceutical active(s) is dissolved in, or forms a eutectic with, the molten aliphatic or fatty acid ester prior to solidifying or the pharmaceutical active(s) is suspended in molten aliphatic or fatty acid ester prior to solidifying.

In other embodiments of the inventions a solventless method for preparing a pharmaceutical matrix is provided comprising the steps of: melting an aliphatic or fatty acid ester; admixing at least one pharmaceutical active with molten aliphatic or fatty acid ester; and spray congealing the admixture to produce a pharmaceutical matrix powder of the aliphatic or fatty acid ester and pharmaceutical active(s). In preferred embodiments the aliphatic or fatty acid ester is selected from the group consisting of aliphatic fatty acid esters, with melting points in the 50°-100° C. range; more preferably stearyl stearate. In other preferred embodiments the pharmaceutical active(s) are either dissolved, forms an eutectic, or suspended in the molten aliphatic ester prior to spray congealing.

These physiochemically stable matrices may be used for intact tablets or fine powders (<100 microns). These fine powders can be incorporated into various dosage forms and drug delivery systems.

In further embodiments of the invention, a solventless method for preparing a coated taste masked pharmaceutical is provided comprising the steps of: melting an aliphatic or fatty acid ester; coating at least one pharmaceutical active with the molten aliphatic or fatty acid ester; and forming a coated taste masked pharmaceutical composition. In preferred embodiments of the method of the invention the aliphatic or fatty acid ester is selected from the group consisting of aliphatic or fatty acid esters, with melting points in the 50°-100° C. range; more preferably stearyl stearate. In preferred embodiments of the invention the pharmaceutical active(s) is dissolved in, or forms a eutectic with, the molten aliphatic or fatty acid ester prior to solidifying or the pharmaceutical active(s) is suspended in molten aliphatic or fatty acid ester prior to solidifying. In preferred methods of the invention the pharmaceutical active is coated utilizing a fluid bed or Wurster coating apparatus.

The invention also provides a solid dosage form comprising a discrete pharmaceutical active coated or combined with a taste masking or matrix forming effective amount of an aliphatic or fatty acid ester which is formed into powder or pellets and pressed into a tablet or caplet dosage form. In further preferred embodiments tableting excipients may be added to provide desired characteristics to the dosage form including binders to provide strength and/or hardness or wicking or disintegrating agents to hasten dissolution of the tablet or caplet and quicken the release of pharmaceutical active therefrom.

DETAILED DESCRIPTION OF THE INVENTION

The invention will now be described specifically in terms of its most preferred embodiments which concerns the preparation of carrier matrices and spray congealed powders comprising an admixture of aliphatic or fatty acid esters and pharmaceutical actives which can be compressed into tablet and caplet dosage form for swallowing and/or chewing as well as added to liquid suspensions that can be used in both over-the-counter and prescription drug products. Reference will also be made in detail herein to other preferred embodiments of the compositions, processes and methods of the invention including specific illustrative examples.

In preferred embodiments of the composition of the invention, a taste mask coating or carrier matrix for pharmaceutical active(s) is provided which comprises a taste masking or matrix forming effective amount of an aliphatic or fatty acid ester. An effective amount is that amount which produces the desirable function, i.e. either taste masking or matrix forming of pharmaceutical active(s). Coating as defined herein refers to a matrix forming step as distinguished from an encapsulating process.

Aliphatic or fatty acid esters in accordance with the invention are stable in that they do not form polymorphs upon aging or otherwise decompose or change their form upon aging. Aliphatic or fatty acid esters are for the most part taste-neutral or have a bland waxy taste and will provide good taste masking characteristics to pharmaceutical actives coated therewith. Aliphatic or fatty acid esters useful in accordance with the invention are solids at room temperatures and have melting temperatures preferably in the range of about 50° to 100° C.

Examples of useful aliphatic or fatty acid esters in accordance with the invention include esters of fatty acids and alcohols. More preferably aliphatic or fatty acid esters useful in accordance with the invention are selected from the group consisting of aliphatic or fatty acid esters, with melting points in the 50°-100° C. range; more preferably stearyl stearate. Examples of suitable aliphatic esters, or fatty acid esters, include stearyl stearate. The most preferred aliphatic ester in accordance with the invention is stearyl stearate which is a solid at room temperature but has a melting point of about 56° C.

The fact that the aliphatic or fatty acid esters in accordance with the invention are a solid at room temperature and melt at relatively low temperatures provides an ideal medium for providing a solventless coating system. In accordance with the invention, aliphatic or fatty acid esters are melted and pharmaceutical actives, which are stable at the molten temperatures of such aliphatic or fatty acid esters, are admixed with the molten ester to provide either a solution or a suspension of such pharmaceutical actives within the ester melt. The admixture of aliphatic or fatty acid ester and pharmaceutical active is then solidified either by simple cooling or by spray congealing to form aliphatic or fatty acid ester coated pharmaceutical active (e.g. powders) or matrices of aliphatic or fatty acid esters and pharmaceutical actives.

Aliphatic or fatty acid esters themselves are poorly soluble or insoluble in water and may inhibit ready release of the coated pharmaceutical actives. Addition of water soluble additives may increase the release rate of the coated pharmaceutical actives by providing a soluble portion to the coating to render it porous, thus permitting permeation of the pharmaceutical active therefrom. For example, water soluble additives for hastening release may include conventional pharmaceutical excipients including polymers (e.g. polyethylene glycol, hydroxypropyl methyl cellulose, polyvinylpyrrolidone); sugars (e.g. sucrose, dextrose, sorbitol, mannitol); and salts (e.g. KCl, NaCl). Other pharmaceutical excipients may be added to the melt to aid in processing (e.g. silicon dioxide, surfactants).

The aliphatic or fatty acid ester-coated pharmaceutical actives may be used in various oral, rectal, vaginal or external preparations and may provide for altering the release rate, taste or stability characteristics of such dosage forms. The aliphatic or fatty acid ester coating may contribute to enhance the physicochemical stability of the pharmaceutical actives particularly where such actives are unstable upon exposure to air or low to high moisture conditions, Further, the use of molten aliphatic or fatty acid esters as a coating or carrier for pharmaceutical actives may improve the material's physical properties in terms of bulk handling and flow.

The coated pharmaceutical products produced using aliphatic or fatty acid esters in accordance with the invention generally have drug to coating ratios of about 5:95 to 50:50. Pharmaceutical matrix products produced using aliphatic or fatty acid esters as a carrier material in accordance with the invention generally have drug to carrier ratios which are suitable for their particular application, e.g., taste masking. The higher ratios are particularly useful for swallowable, rectal and externally applied dosage forms where taste masking is not required.

The lower ratios are generally applicable to taste masked preparations to shield the taste of the pharmaceutical active from the consumer or patient. The drug:coating/carrier ratio will also vary with the dosage amounts of pharmaceutical actives whereby low dosage pharmaceuticals like loperamide HCl may have a low ratio of drug to carrier/excipient to provide bulk to the dosage form. A higher dosage amount of a pharmaceutical like acetaminophen may in contrast be provided in higher ratios of drug to carrier/excipient composition to reduce the size of the dosage form, particularly for ease of swallowing.

An advantageous feature of aliphatic or fatty acid esters as a pharmaceutical carrier is its waxy, non-gritty feel. This characteristic is advantageous to most dosage forms but particularly when applied to chewable, rectal and externally applied dosage forms. Further, a smooth waxy feel of a dosage form contributes to its ease of swallowing.

Spray congealed particles or matrices of pharmaceutical actives and aliphatic or fatty acid esters are particularly useful for taste masking applications because the small size of the spray congealed particles will avoid the mechanical action of chewing and remain intact while in the mouth.

Such particles or powders are produced by feeding a solution or suspension of pharmaceutical active(s) in a melt of aliphatic ester through a nozzle at pressures sufficient to atomize the melt. The atomized melt will congeal and form small droplets. The size of the droplets can be controlled by the type of nozzle and/or atomization pressure. External air may be applied to the melt as it exits the nozzle to control the size and cooling rate of the spray congealed particles. The temperature of the air is maintained below the congealing point of the melt for such applications. Conventional spray drying equipment may be modified to accommodate the required temperature control for spray congealing the melt into fine particles.

Pharmaceutical matrices may also be prepared from a solution or suspension of pharmaceutical active(s) in a melt of aliphatic or fatty acid ester by compression, hot melt injection molding or extruding of the solidified mixture. Coated particles of pharmaceutical active may be made by applying molten aliphatic or fatty acid ester to pharmaceutical active in a fluid bed apparatus through top or bottom spray methods or Wurster coating apparatus. The molten coating may be top sprayed onto the pharmaceutical active or actives granulation in a conventional fluid bed apparatus. The melt will coat the particles and/or granulates of the pharmaceutical active. The coating of individual particles may be more efficient using a Wurster insert in the fluid bed apparatus. If the process parameters are adequately controlled the coating of individual particles is maximized, and aggregation or agglomeration of the individual particles is minimized. The formation of coated particles or coated granulation may be achieved in other fluid bed granulators or coaters (i.e. rotogranulator).

Preferred pharmaceutical actives useful in accordance with the aliphatic or fatty acid esters of the invention are those which remain stable above the melting temperatures (e.g., about 10° C. above the melting point) of the aliphatic or fatty acid esters utilized. Illustrative examples of pharmaceutical actives which may be useful in accordance with the invention include but are not limited to analgesics, antihistamines, decongestants, cough suppressants, antacids, antidiarrheals, antidepressants etc. Particularly preferred actives include acetaminophen, ibuprofen, pseudoephedrine HCl, chlorpheniramine maleate, dextromethorphan HBr, and loperamide HCl and their pharmaceutically acceptable salts.

EXAMPLES

The following procedure and examples are illustrative of the preferred methods and materials for practicing the present invention. These examples should be considered illustrative only and not limitative of the present invention.

EXAMPLE 1

Aliphatic ester (stearyl stearate) is melted at approximately 75°–95° C. Acetaminophen, 20–50% by weight, is added to the molten aliphatic ester. The suspension is mixed, pumped and sprayed into a collection chamber. A fine powder is collected. Samples were stored for at least 2 weeks. Samples were tested for polymorphic changes by Differential Scanning Calorimetry and Powder X-Ray Diffraction. No polymorphic changes had occurred.

EXAMPLE 2

To prepare coated acetaminophen, aliphatic ester (stearyl stearate) is melted at approximately 75° C. The molten solution is sprayed into a fluidized bed of acetaminophen crystals or granules. Any of top spray coating, down spray coating, Wurster coating or rotogranulator coating equipment can be used to coat the acetaminophen. Individual crystals, granulation or granules may be coated for taste masking by this method.

EXAMPLE 3

Poorly water soluble loperamide HCl 10–50% by weight of the total composition was substituted for acetaminophen in Example 1 and admixed with stearyl stearate for immediate release applications and taste masking applications.

EXAMPLE 4

Poorly water soluble ibuprofen, 20–50% by weight, was substituted for acetaminophen as in Example 1 and mixed with stearyl stearate for immediate release applications and taste masking.

EXAMPLE 5

Highly water soluble pseudoephedrine HCl was substituted for acetaminophen in Example 1 and coated with stearyl stearate for immediate release and taste masking applications.

EXAMPLE 6

Powder from Example 1 was incorporated into a chewable tablet formulation. The stearyl stearate-acetaminophen powder was mixed with suitable excipients commonly found in chewable dosage forms and made into tablets using pharmaceutical compression equipment. A taste masked chewable tablet resulted from the formulation below.

| Ingredient | mg/tablet | % |
| --- | --- | --- |
| Composition | | |
| Coated acetaminophen (40:60 acetaminophen/ stearyl stearate weight by weight) | 200 (80 mg acetaminophen 120 mg stearyl stearate) | 43–52 |
| Mannitol/Sorbitol | 150–200 | 39–43 |
| Microcrystalline cellulose | 30–50 | 8–11 |
| Sweeteners | 0.1–5.0 | 0.02–1.3 |
| Flavors | 0.1–5.0 | 0.02–1.3 |
| Colors | 0.002–0.0002 | 0.0005–0.00005 |
| Magnesium stearate | 3–5 | 0.8–1.3 |

EXAMPLE 7

Powder from Example 1 was incorporated into a oral suspension formulation. The stearyl stearate-acetaminophen powder was formulated into an oral suspension using ingredients commonly found in oral pharmaceutical suspensions. A taste masked suspension resulted.

EXAMPLE 8

Coated granules, granulation or crystals from Example 2 were incorporated into a chewable tablet formulation. The stearyl stearate-acetaminophen powder was mixed with suitable excipients commonly found in chewable dosage forms and made into tablets using pharmaceutical compression equipment. A taste masked chewable tablet resulted.

EXAMPLE 9

Powder from Example 3 was incorporated into a chewable tablet formulation. The stearyl stearate-loperamide HCl powder was mixed with suitable excipients commonly found in chewable dosage forms and made into tablets using pharmaceutical compression equipment. A taste masked chewable tablet resulted.

EXAMPLE 10

Powder from Example 4 was incorporated into an oral suspension formulation. The stearyl stearate-ibuprofen powder was formulated into an oral suspension using ingredients commonly found in oral pharmaceutical suspensions. A taste masked suspension resulted from the formulation below.

| Ingredient | mg/5 ml | gm % |
| --- | --- | --- |
| Coated ibuprofen (50:50 ibuprofen: stearyl stearate weight by weight) | 200 mg (100 mg ibuprofen and 100 mg stearyl stearate) | 4.0 |
| suspending agents | 25–100 | 0.5–2.0 |
| Glycerin/Sorbitol | 250–1500 | 5–30 |
| Sucrose/Fructose | 500–1500 | 10–30 |
| Surfactant | 2.5–10 | 0.05–0.2 |
| Flavors | 25 mg | 0.5 |
| Preservative | 10 mg | 0.2 |
| Water, qs | 5 ml | 100 |

EXAMPLE 11

Powder from Example 4 was incorporated into a chewable dosage form. The stearyl stearate-ibuprofen powder was mixed with suitable excipients commonly found in chewable dosage forms and made into tablets using pharmaceutical compression equipment. A taste masked chewable tablet resulted.

EXAMPLE 12

Powder from Example 5 was incorporated into a chewable dosage form. The stearyl stearate-pseudoephedrine HCl powder was mixed with suitable excipients commonly found in chewable dosage forms and made into tablets using pharmaceutical compression equipment. A taste masked chewable tablet resulted.

EXAMPLE 13

Glyceryl mono,di, or tribehenate is substituted for stearyl stearate in Example 1.

Further, combinations of pharmaceutical actives, such as acetaminophen and pseudoephedrine, can be mixed with molten aliphatic ester in accordance with the procedure of Example 1 to achieve taste masking of both components.

The scope of the present invention is not limited by the description, examples and suggested uses herein and modifications can be made without departing from the spirit of the invention. For example, other components may be added to the tablets including additional actives, various flavorings, preservatives and other pharmaceutical excipients. The present invention may be applied to dosage forms or drug delivery systems other than the chewable tablets or oral suspensions mentioned in the example section. These may include suppositories, creams, ointments, aerosols and incorporation into drug delivery systems such as transdermal, buccal, ocular, vaginal or nasal delivery systems. Also included would be incorporation of the powder into newly evolving fast acting and slow acting dosage forms or delivery devices. The present invention may also be applied to provide a sustained release, chewable and/or physicochemical stable form for vitamins, minerals or other nutrients or for flavorings in food items. Further, the present invention may have agricultural applications for delivery of pesticides or fertilizers.

Application of the compositions and processes of the present invention for medical and pharmaceutical uses can be accomplished by any clinical, medical and pharmaceutical methods and techniques as are presently and prospectively known to those skilled in the art. Thus it is intended that the present invention cover the modifications and variations of this invention provided that they come within the scope of the appended claims and their equivalents.

What is claimed is:

1. A solventless method for preparing a solid pharmaceutical matrix consisting of the steps of:
   melting stearyl stearate;
   admixing at least one pharmaceutical active with the molten stearyl stearate; and
   spray congealing the admixture under conditions suitable to form a powder having a particle size less 100 microns to produce a solid pharmaceutical matrix powder of the stearyl stearate and pharmaceutical active.

2. The method of claim 1 wherein the pharmaceutical active is dissolved in, or forms a eutectic with, the molten stearyl stearate prior to solidifying.

3. The method of claim 1 wherein the pharmaceutical active is suspended in the molten stearyl stearate prior to solidifying.

4. A solventless method for preparing a coated pharmaceutical active composition consisting of the steps of:
   melting stearyl stearate and
   coating a pharmaceutical active composition with the molten stearyl stearate to form a powder having a particle size less than 100 microns.

5. The method of claim 4 wherein the coating step is carried out utilizing a fluid bed coating process.

6. A physicochemically stable powder having a particle size of less than 100 microns consisting of a solid matrix of a pharmaceutical active and stearyl stearate.

7. The powder of claim 6 wherein the stearyl stearate is provided in an amount effective to taste mask the pharmaceutical active.

8. The pharmaceutical active of claim 6 wherein the active is selected from the group consisting of acetaminophen; ibuprofen; pseudoephedrine HCl; chlorpheniramine maleate; dextromethorphan; and loperamide HCl.

9. The pharmaceutical active of claim 6 wherein the active is a mixture of acetaminophen and pseudoephedrine HCl.

10. A solid oral dosage form consisting of a physicochemically stable powder having a particle size of less than 100 microns composed of a solid matrix of a pharmaceutical active stearyl stearate and tableting excipients formed into a tablet or caplet.

11. An orally administrable dosage form, consisting of:
    at least one pharmaceutical active coated with stearyl stearate wherein the weight ratio of pharmaceutical active to coating is about 5:95 to about 50:50; and
    pharmaceutically acceptable excipient.

12. The dosage form of claim 11 in the form of a solid.

13. The dosage form of claim 11 in the form of a liquid suspension.

14. The dosage form of claim 11 wherein the active is selected from the group consisting of acetaminophen, ibuprofen, pseudoephedrine HCl, chlorpheniramine maleate, dextromethorphan, and loperamide HCl.

* * * * *